(12) United States Patent
Pross

(10) Patent No.: US 6,568,254 B2
(45) Date of Patent: May 27, 2003

(54) METHOD FOR MONITORING THE CREEP BEHAVIOR OF ROTATING COMPONENTS OF A COMPRESSOR STAGE OR TURBINE STAGE

(75) Inventor: Jörg Pross, Albbruch (DE)

(73) Assignee: Alstom (Switzerland) Ltd, Baden (CH)

( * ) Notice: Subject to any disclaimer, the term of this patent is extended or adjusted under 35 U.S.C. 154(b) by 139 days.

(21) Appl. No.: 09/747,943

(22) Filed: Dec. 27, 2000

(65) Prior Publication Data

US 2002/0019708 A1 Feb. 14, 2002

(30) Foreign Application Priority Data

Dec. 23, 1999 (DE) .......................... 199 62 735

(51) Int. Cl.⁷ .............................................. G01M 15/00
(52) U.S. Cl. ........................... 73/116; 73/117.4; 73/822
(58) Field of Search .................. 73/35.12, 37, 115, 73/117.3, 766, 783, 787, 822, 826, 861.19, 865.8, 865.9, 799, 117.4, 116

(56) References Cited

U.S. PATENT DOCUMENTS 4,768,383 A * 9/1988 Koyama et al. .............. 73/787
5,042,295 A * 8/1991 Seeley ........................ 73/117.3

FOREIGN PATENT DOCUMENTS

| DE | 31 20 653 | 12/1982 |
|----|-----------|---------|
| DE | 36 31 153 | 3/1988 |
| DE | 41 34 743 | 4/1993 |
| DE | 43 34 799 | 4/1995 |
| GB | 2 290 619 | 1/1996 |
| JP | 61-89539 | 5/1986 |
| JP | 61-172059 | 8/1986 |
| JP | 62-835 | 1/1987 |
| JP | 10-123123 | 5/1998 |
| JP | 11-248605 | 9/1999 |

* cited by examiner

Primary Examiner—Eric S. McCall
(74) Attorney, Agent, or Firm—Burns, Doane, Swecker & Mathis, L.L.P.

(57) ABSTRACT

The present invention relates to a method for monitoring the creep behavior of rotating components of a compressor stage or turbine stage. In the method, at least one test element (2) is mounted in a region of the compressor stage or turbine stage in which the test element is exposed to an operating load comparable to that of the component to be monitored. The test element (2) is investigated after a predeterminable operating period of the component to be monitored. Finally, the creep behavior of the component to be monitored is derived from the creep behavior of the test element.

The method makes it possible to detect exactly the creep behavior or creep damage of the component to be monitored, during the useful life of this component.

18 Claims, 2 Drawing Sheets

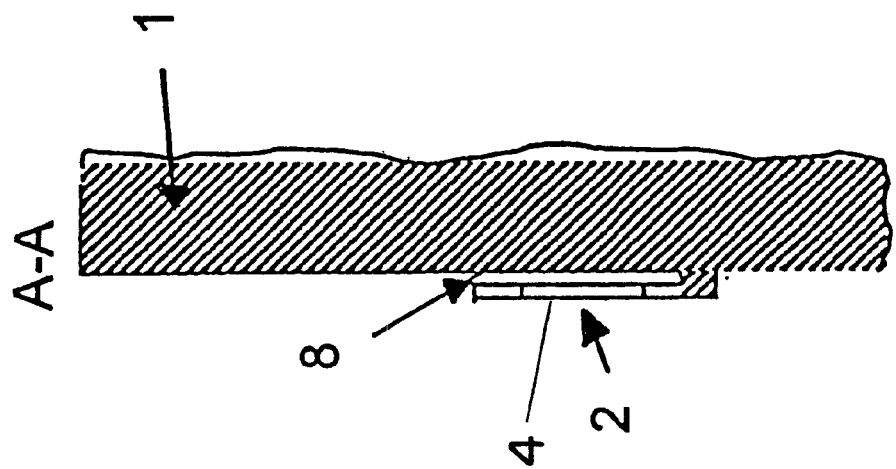
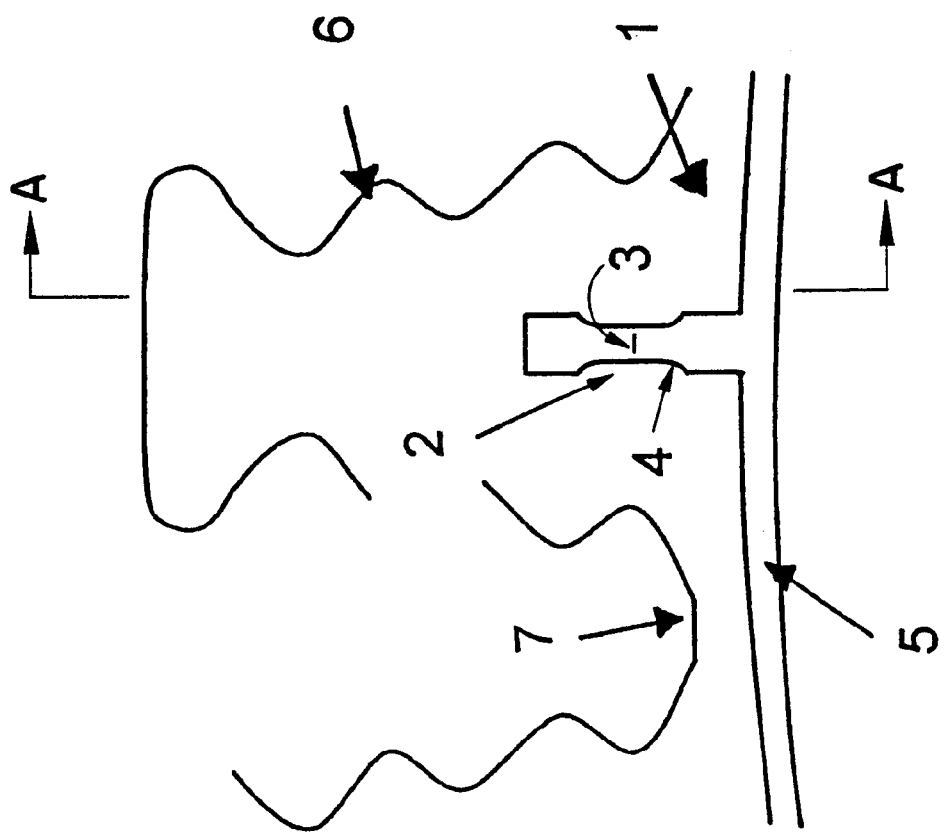

METHOD FOR MONITORING THE CREEP BEHAVIOR OF ROTATING COMPONENTS OF A COMPRESSOR STAGE OR TURBINE STAGE

FIELD OF THE INVENTION

The present invention relates to a method for monitoring the creep behavior of rotating components of a compressor stage or turbine stage, such as are used, for example, in gas turbines.

BACKGROUND OF THE INVENTION

The rotors and moving blades of stages of this type are exposed to high mechanical load by centrifugal forces and to a very high temperature. The temperatures are, as a rule, above the transition temperature of the materials, so that time-dependent plastic expansion, so-called creeping, constitutes an essential factor limiting the useful life of the respective components.

It is therefore an important task, in the operation of a plant, to determine the creep behavior or the remaining useful life of costly components of a turbine, such as rotors and moving blades. In this context, on the one hand, safety aspects, and, on the other hand, financial aspects play an important part. Thus, a very late exchange of the components leads to a high safety risk within the plant, while too early an exchange of the components entails unnecessary costs. It is therefore very important, during the operation of a plant of this type, to monitor and estimate the creep behavior of rotating components in compressor stages and turbine stages and to estimate correctly the remaining useful life of these components.

At the present time, the creep life of turbine components is determined, as a rule, by means of the Finite Element Method (FEM), using viscoplastic material models. However, models of this type require an accurate knowledge of the material constants, boundary conditions and operating conditions, to which the components are subjected during operation. The accuracy of prognosis of these computational models is very limited because of the uncertainties in the specification of these parameters. Thus, the external boundary conditions, in particular the material temperatures during operation, cannot always be specified with sufficient accuracy. On the other hand, in particular, the material temperature has an appreciable influence on the results. Another uncertainty factor is found in the available data on the creep behavior of the material. The material composition in the production of the components is subject to variations which may, in turn, lead to different creep behaviors of the material of the component. It is not possible, because of these variations, to know the exact data relating to the creep behavior of the material of the very component to be monitored.

Finally, the development in time of creep damage is also dependent on the respectively preceding development in time of the force load and temperatures, that is to say on the previous history of the component. An exact prognosis of the creep life of a component used during operation would therefore require a simulation of the actual operating cycles of the plant. This is virtually impossible, however, because of the multiplicity of influences involved, such as hot or cold ambient conditions, transient operation, etc. The purely computational prognosis of the creep life of a component therefore does not lead to satisfactory results.

An improvement in prognosis can be achieved by the prognosis being checked by means of concrete measurements of the creep damage of the monitored component after various operation periods and, if appropriate, being corrected by adaption of the parameters. This makes it necessary, however, to determine the creep behavior or creep damage of the component by means of nondestructive test methods.

At the present time, however, there are no nondestructive test methods available which could provide reliable evidence on the creep damage of a component at an early operational stage.

Thus, admittedly, the so-called replica technique is known, in which conclusions as to microstructural damage can be drawn from an impression of the component surface or of parts thereof. However, this damage is often detected only in the so-called tertiary creep stage, that is to say at a time when the turbine components should have long since been taken out of service.

Another technique often used for determining the creep behavior of a component is the measurement of the dimensions of the component. This dimension changes due to the accumulation of inelastic expansions during the operating period. By comparing the dimensional changes with the computational results, corrections can likewise be made to the computing parameters in this way. One disadvantage of this technique, however, is that only overall creep damage of relatively large components can be detected with it, since the dimensional changes must have a measurable magnitude. This necessitates either large accumulated creep expansion or a correspondingly large length or dimension of the component.

In a further technique, test material is extracted from the component after a specific operating period and is investigated. However, this test material can be extracted only from places which have no influence on the further operating behavior of the component. These are regions with low stresses or without appreciable stresses, so that, although this test material has been exposed to the same temperatures as the component, it has not been subjected to any loads which are relevant to useful life. It is therefore scarcely possible to demonstrate creep damage on such testpieces, with the result that this technique supplies information for correcting the computational models to only a very limited extent.

Other nondestructive test methods, such as are used in other technical sectors, also do not at the present time supply any satisfactory results for evaluating creep damage. Thus, discontinuities in the material can be detected by ultrasound or magnetic methods. Even here, however, evidence of creep damage or of further behavior again requires the use of new computer models, such as are proposed, for example, in U.S. Pat. No. 5,140,528.

In summary, there have hitherto been no satisfactory methods for either monitoring or determining the remaining creep life of a rotating component of a turbine stage or compressor stage.

SUMMARY OF THE INVENTION

An object of the invention is to provide a method for monitoring the creep behavior of rotating components of a compressor stage or turbine stage, by means of which the creep behavior or creep damage of the component to be monitored can be detected with higher accuracy than hitherto. The method is to make it possible, in particular, to detect the creep damage at various times during the useful life of the component.

The object is achieved by the method according to the invention, wherein at least one test element is mounted in a region of the compressor stage or turbine stage in which said test element is exposed to an operating load comparable to that of the component to be monitored. By operating load are to be meant here, in particular, the forces acting on the component, for example the centrifugal force, and the temperatures to which the component is exposed during operation. After a predeterminable operating period of the component to be monitored, the creep behavior of the test element is investigated. The creep behavior or creep damage of the component to be monitored is derived from the creep behavior or creep damage of the test element determined in this way. These data may subsequently be compared with a computational model, so that the parameters of the model can be corrected accordingly.

It goes without saying that the test element is mounted in the turbine stage or compressor stage in such a way that said test element does not impair the operation and functioning of the latter. For this purpose, it is necessary, on the one hand, for the test element to have a correspondingly low weight and, on the other hand, to be provided at a point where it does not disturb the flow conditions within the turbine stage or compressor stage.

The one or more test elements are exposed to the same operating cycles as the component itself while the component is in operation. At the same time, the test elements are provided in a suitable form which makes it possible for them to be exposed to forces comparable to those of the component itself. This may be achieved, in terms of the load due to centrifugal forces, by means of an elongate form of the test element, in that the latter is mounted at one end on the rotating body, for example the rotor. In this case, the centrifugal force that is acting on the test element can be predetermined by the form of the test element.

Furthermore, a suitable connection of the test element to the integral parts of the turbine stage or the compressor stage should ensure that creep damage of the test element cannot be transferred to parts of the turbine stage or compressor stage.

The method according to the invention affords the advantage that the component to be monitored and the test element or test elements are operated under the same temperature conditions. The uncertainties, such as arise in terms of the temperature parameters when computational models are used for determining the creep damage of a component, can be avoided by means of the present method. Moreover, the test elements can be coordinated exactly with the respective method of investigation which is used to detect measurable creep damage. With this method, the component to be monitored does not have to be investigated. The uncertainties in the actual operating conditions are ruled out, so that more accurate results can be achieved than are possible with the methods known hitherto. These results may, in turn, serve for correcting a model computation carried out in parallel in order to determine the remaining creep life of the component.

In a preferred embodiment of the method according to the invention, the test element is manufactured from the same material batch from which the component to be monitored was manufactured. Precisely the abovementioned variations in the materials and the associated uncertainties in the material parameters can thereby be ruled out. In this embodiment, the test elements are therefore manufactured preferably at the same time as the components themselves.

The test element or test elements may also be manufactured from a material which has a creep behavior more pronounced than that of the material of the component. Possible damage can thereby be detected more quickly. A precondition for this embodiment, however, is that a concrete relationship between the creep behavior of the material of the test element and the creep behavior of the material of the component to be monitored is ensured and is known.

The test element is fastened preferably directly to the component to be monitored, such as, for example, the rotor or the blade. Thus, the test element can be manufactured integrally with this component. The advantage of this is that the component and test element consist of exactly the same material. Furthermore, an additional method step for mounting the test element on the component is avoided.

If, however, the test element is to be mounted only after the component has been produced, this is carried out preferably by means of a welding method. In this case, however, care must be taken to ensure that refusion zones produced as a result of welding do not impair either the regions of the test element which are to be investigated or the component itself. Even when the test element is mounted later, the best results are achieved if the latter is manufactured from the same material batch as the component to be monitored. In addition to welding, of course, other methods for connecting the test element to structural parts of the turbine stage or compressor stage are also possible. The type of connection depends here, in particular, on the loads on the connecting seam which are to be borne. The test element also does not have to be fastened directly to the component to be monitored, but may also be provided on adjacent structural parts. Thus, in order to monitor the creep behavior of a moving blade, the test element could also be fastened to the rotor, for example by means of mechanical suspension in a circumferential groove on the rotor.

There are various possibilities for investigating the test element in terms of creep damage or creep behavior. Thus, the dimensions of the test element could be measured, in order, for example, to make it possible to demonstrate a change in length. In this case, the form of the test element is selected such that dimensional changes can easily be demonstrated. Thus, the test element used is preferably an element with an elongate flat form and with a tapered portion. A dimensional change can, in this case, be detected easily by means of the ratio of the width of the ends to the tapered portion.

In a further preferred embodiment, the test element is provided from the outset with an artificial crack, of which the change, in particular lengthening, widening or instability, is monitored. Characteristic values for the models of the basic fracture mechanics can be obtained from the observation of the behavior of this crack.

It goes without saying that, in practice, investigation of the test element or test elements is carried out not only once after a specific operating period, but at different operating periods, so that the development in time of the material stress can be detected in this way. During each detection, the behavior of the component to be monitored is derived from the behavior of the test element and, preferably, corresponding computer simulations carried out at the same time are matched with or corrected by means of the newly acquired data.

In a further preferred embodiment, not only a single test element but a plurality of test elements are used for monitoring the component. This allows an even more detailed investigation of the creep damage of the component to be monitored. Thus, in each case after a specific operating period, a test element is removed from the turbine stage and compressor stage. This test element can subsequently undergo any desired material tests. In this context in particular, metallographic test methods for investigating a change in the structure, a direct measurement of the remaining useful life by means of corresponding mechanical stress, the checking of the expansion limit by means of tensile load or the like come under consideration. In turn, the parameters of a model computation for determining the creep life can be adapted from these data.

By the provision of a plurality of test elements, a test element can be detached and investigated in this way whenever the plant is inspected. It is, of course, also possible, during each inspection, to detach a plurality of test elements simultaneously and deliver them for different investigations. It is also advantageous, in this respect, if test elements with a different configuration, that is to say a different form and different material properties, are used, which are in each case coordinated with the method of investigation to be carried out. At the same time, additional data may be acquired during an inspection.

BRIEF DESCRIPTION OF THE DRAWINGS

A preferred embodiment of the invention is described below, with reference to the accompanying drawings, in which:

FIG. 1 is a schematic view of a test element and the mounting of the latter on a rotor disk to be monitored;

FIG. 2 is a cross-sectional view of the test element and rotor disk along the line A—A in FIG. 1.

DETAILED DESCRIPTION OF THE INVENTION

Figure 3:
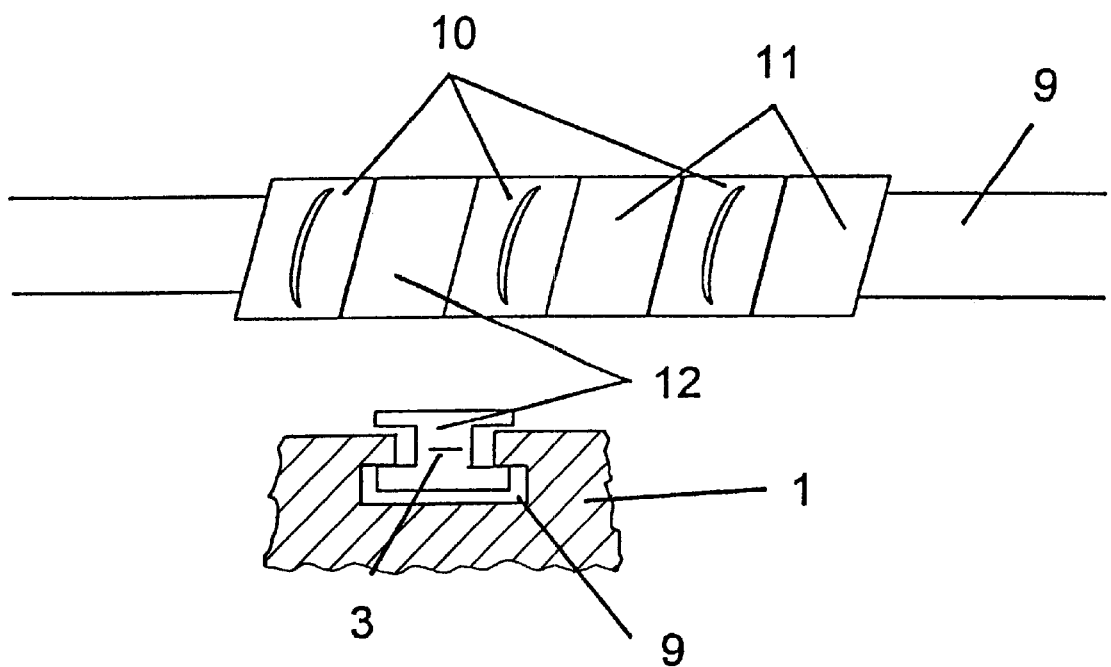
FIG. 3 is a detail view of the mechanical suspension of a test element on a rotor.

In the following description, the rotor disk of a turbine stage is to be monitored in terms of creep behavior. FIG. 1 shows, in this context, the rotor disk 1 with the test element 2 fastened to it. In this example, the test element has an elongate flat form with a tapered portion 4. The test element is fastened at one end to a peripheral ring 5 projecting on the side face of the rotor.

In the present case, the test element is arranged in front of the fastening pin 6 for the axial moving blades. The blade recess 7 can be seen between two fastening pins. The peripheral ring is manufactured integrally with the rotor. The test element can be fastened, for example welded, to the ring later. However, it may also be directly produced integrally with the rotor disk. In this case, a narrow gap 8 necessary between the rotor disk and the test element may be worked out by means of an erosion method.

The separation between the test element and the side face of the rotor disk 1 by means of the gap 8 is necessary, on the one hand, in order to ensure that the test element is subjected through its own mass to the centrifugal force and is not supported by the rotor disk. On the other hand, this gap 8 prevents damage to the test element from being continued in the rotor disk. The gap 8 can be seen clearly in FIG. 2 which illustrates a section along the line A—A of FIG. 1.

By virtue of the form of the test element 2 with the tapered portion 4, the load on the test element can easily be checked by means of the ratio between the wider ends and the tapered portion. In this example, the test element was provided from the outset with an artificial crack 3, of which the development or extent can be detected during each inspection of the rotor 1. The configuration of this crack is, in this case, preferably selected such that the C integral, which occurs in theoretical models of fracture mechanics and describes the viscoplastic stress field at the crack tip, can be calculated without much effort. This calculation may be refined by correcting the parameters on the basis of the data detected during each inspection.

In order to ensure even stress conditions, the test element can be made very thin so that its mounting requires scarcely any additional space.

Furthermore, as a result of this flat design, the additional rotor load caused by the test element, and also a possible unbalance induced thereby, may be ignored. The possible unbalance may also be prevented by a plurality of test elements being fastened to the rotor disk in an equal distribution along the peripheral ring. By a plurality of test elements being provided, additional information on the material behavior may be acquired at the same time.

The method according to the invention may be used on all rotating components of compressor stages and turbine stages. The dimensions of the test element, which, in the present example, has a width of about 10–15 mm and a length of about 20–40 mm, depend on the size ratios of the respective components and can be selected appropriately at any time by a person skilled in the art. The same applies to the form of the test element and to the mounting location.

Finally, FIG. 3 shows a further example of the mounting of a test element on a rotor disk 1. Here, the rotor disk has a circumferential groove 9, into which the moving blades 10 are suspended. Intermediate pieces 11 are introduced in each case between the moving blades of a blade row. In this example, the test element is designed as an intermediate piece 12 and is suspended into the blade row instead of a normal intermediate piece 11. The upper part of the drawing shows a top view of the arrangement in this case, and the lower part shows a section through the circumferential groove 9 at the position of the test element 12. In this case, the test element 12 designed as an intermediate piece is suspended mechanically in the circumferential groove 9 in the same way as the normal intermediate pieces 11. The artificial crack 3, with which the test element 12 is provided in this example, can also be seen in the lower part of FIG. 3.

The test element 12 may consist of a different material from or the same material as the remaining blades and intermediate pieces. Either the creep behavior of the blade row or that of the rotor can be monitored by means of a suitable choice of the material for the test element.

What is claimed is:

1. A method for monitoring a creep behavior of rotating components of a compressor stage or turbine stage, the method comprising the steps of:

mounting at least one test element in a region of the compressor stage or turbine stage in which said test element is exposed to an operating load comparable to that of the component to be monitored;

investigating the creep behavior of the test element after a predetermined operating period of the component to be monitored; and deriving the creep behavior of the component to be monitored from the creep behavior of the test element.

2. The method as claimed in claim 1, wherein both the test element the component to be monitored are manufactured from one material.

3. The method as claimed in claim 1, the method further comprising making an artificial crack in the test element, from the development of which the creep behavior of the component to be monitored is derived.

4. The method as claimed in claim 1, wherein the test element has an elongate flat form with a tapered portion.

5. The method as claimed in claim 1, the method further comprising: mounting the test element on the component to be monitored.

6. The method as claimed in claim 5, wherein the mounting of the test element takes place during the production of the component to be monitored, in that said test element is manufactured integrally with the component to be monitored.

7. The method as claimed in claim 1, wherein the operation of mounting of the test element further comprises welding the test element in the region of the compressor stage or the turbine stage.

8. The method as claimed in claim 1, wherein the mounting of the test element is carried out my means of mechanical suspension.

9. The method as claimed in claim 1, including investigating the creep behavior of the test element is carried out by the measurement of a dimensional change in the test element.

10. The method as claimed in claim 1, including investigating the creep behavior of the test element by detaching the test element from the component to be monitored and by subsequently destructively testing the test element.

11. The method as claimed in claim 1, wherein the test element is destroyed when a predeterminable creeping range is exceeded.

12. The method as claimed in claim 1, the method further comprising mounting a plurality of test elements on the component to be monitored and investigating the creep behavior of the plurality of test elements.

13. The method as claimed in claim 12, wherein at least one of the plurality of test elements are investigated after a different operating period of the component to be monitored.

14. The method according to claim 12, wherein individual test elements of the plurality of test elements have individual geometries, where the individual geometries of the individual test elements of the plurality of the test elements differ from one another.

15. The method according to claim 12, wherein the individual test elements of the plurality of test elements are constructed from differing materials such that the materials of the individual components differ from one another.

16. The method according to claim 15, the method further comprising investigating the plurality of the test elements after the predetermined operating period of the component to be monitored.

17. The method as claimed in claim 1, wherein the component to be monitored is manufactured from a first material and the test element is manufactured from a second material where a creep behavior of the second material is stronger than a creep behavior of the first material.

18. The method according to claim 14, the method further comprising investigating the plurality of the test elements after the predetermined operating period of the component to be monitored.

* * * * *